(12) United States Patent
Mathieu et al.

(10) Patent No.: US 6,399,839 B1
(45) Date of Patent: *Jun. 4, 2002

(54) METHOD FOR PREPARING HALOGENATED HYDROCARBONS

(75) Inventors: Véronique Mathieu, Wavre; Francine Janssens, Vilvoorde, both of (BE)

(73) Assignee: Solvay (Societe Anonyme) (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/423,199

(22) PCT Filed: Apr. 28, 1998

(86) PCT No.: PCT/EP98/02586

§ 371 (c)(1), (2), (4) Date: Nov. 3, 1999

(87) PCT Pub. No.: WO98/50330

PCT Pub. Date: Nov. 12, 1998

(30) Foreign Application Priority Data

May 5, 1997 (BE) ............................................ 09700399
Aug. 8, 1997 (BE) ............................................ 09700669
Feb. 24, 1998 (BE) ............................................ 09800140

(51) Int. Cl.[7] ..................... C07C 17/266; C07C 17/26
(52) U.S. Cl. ........................................ 570/172; 570/257
(58) Field of Search ................................ 570/172, 257

(56) References Cited

U.S. PATENT DOCUMENTS

| | | | |
|---|---|---|---|
| 3,268,603 A | 8/1966 | Scherling | 570/257 |
| 3,454,657 A | 7/1969 | Decker et al. | 260/651 |
| 3,649,698 A | 3/1972 | Goble et al. | 570/257 |
| 3,651,019 A | 3/1972 | Asscher et al. | |
| 3,862,978 A | 1/1975 | Decker et al. | |
| 5,446,217 A | 8/1995 | Van Der Puy et al. | |
| 5,792,893 A | 8/1998 | Wilson et al. | |
| 5,917,098 A | 6/1999 | Bertocchio et al. | |

FOREIGN PATENT DOCUMENTS

| | | |
|---|---|---|
| EP | 0 729 932 | 4/1996 |
| EP | 0 787 707 | 6/1997 |
| FR | 1288511 | 5/1961 |
| GB | 1146463 | 3/1969 |
| GB | 2 188 929 A | 10/1987 |
| WO | 95/04021 | 2/1995 |
| WO | 95/04022 | 2/1995 |
| WO | 96/01797 | 1/1996 |
| WO | 97/05089 | 2/1997 |
| WO | 97/07083 | 2/1997 |
| WO | 97/15540 | 5/1997 |
| WO | 98/50329 | 11/1998 |
| WO | 98/50330 | 11/1998 |
| WO | 99/07659 | 2/1999 |
| ZA | 98/3775 | 1/2000 |
| ZA | 98/3781 | 1/2000 |

OTHER PUBLICATIONS

Asscher and Vofsi, *Chlorine Activation by Redox Transfer, Part II. The addition of Carbon Tetrachloride to Olefins*, 1963, p. 1887–1896.

R. Freidlinda et al., "Telomerization of 2–Chloropropene with Carbon Tetrachloride", Bull. Acad. Sci. USSR, 28, pp. 1766–1769 (1979).

Kotora et al., "Selective Additions of Polyhalogenate Compounds to Chloro Substituted Ethenes Catalyzed by a Copper Complex", React. Kinet. Catal, Lett. 44, No. 2, pp. 415–419 (1991).

Kotora et al., "Addition of Tetrachloromethane to Halogenated Ethenes Catalyzed by Transition Metal Complexes," *Journal of Meolecular Catalysts*, 77:51–60 (1992).

Ullmann's Encyclopedia of Industrial Chemistry, 1992, vol. B4, pp. 387–388.

T. Asahara et al., "Telomerization of Binylchloride with Carbon Tetrachloride Initiated by n–butylamine and Metallic Salts", Kogyo Kagaku Zasshi, 72 pages 1526–29 (1969).

Belbachir et al., "Reaction avec le tetrachlorure de carbone par catalyse redox", Makromol. Chem 185 pp. 1583–1595 (1984).

*Primary Examiner*—Sreeni Padmanabhan
*Assistant Examiner*—Sikarl A. Witherspoon
(74) *Attorney, Agent, or Firm*—Connolly Bove Lodge & Hutz LLP

(57) ABSTRACT

Halohydrocarbons comprising at least 3 carbon atoms are obtained by reaction between a haloalkane and an olefin in the presence of an organocopper compound as catalyst, a solvent and/or a cocatalyst. 1,1,1,3,3-Penta-chloropropane can thus be obtained in good yield under mild conditions.

22 Claims, No Drawings

METHOD FOR PREPARING HALOGENATED HYDROCARBONS

This application is a 371 of PCR/EP98/02586 filed Apr. 28, 1998, now U.S. Ser. No. 98/50330, published Nov. 12, 1998.

The present invention relates to a process for the preparation of halohydrocarbons comprising at least 3 carbon atoms, by catalytic reaction between a halo-alkane and an olefin.

The addition of a haloalkane to an olefin is a well-known reaction. However, it is sometimes difficult to control the reaction such that a single olefin molecule adds to a haloalkane molecule (formation of a 1:1 adduct or addition product).

Very often, copper derivatives are used to catalyse this addition reaction. For example, M. Asscher and D. Vofsi (J. Chem. Soc. 1887–1896, 1963) describe the addition of carbon tetrachloride to olefins in the presence of catalysts containing copper or iron. However, this process has the drawback of requiring long periods of heating in order to obtain the addition product in an acceptable yield.

Patent application WO 97/07083 describes a process for the preparation of halohydrocarbons under the catalytic action of cuprous chloride in the presence of t-butylamine as cocatalyst. In such a process, the yield of telomerization product is still fairly low.

The invention is thus directed towards providing a process which makes it possible to gain access, in excellent yield, to halohydrocarbons comprising at least 3 carbon atoms, in a single step and starting with readily available reagents.

Consequently, the present invention relates to the preparation of halohydrocarbons comprising at least 3 carbon atoms, by reaction between a haloalkane and an olefin in the presence of
- (a) an organocopper compound as catalyst; and
- (b) a polar solvent and/or a cocatalyst chosen from amines, amides and trialkylphosphine oxides.

The organocopper compound used as catalyst in the process according to the present invention is preferably a compound formed with an organic acid compound. Carboxylic acids such as formic acid, acetic acid, propionic acid, butyric acid, acetylacetic acid, cyclo-hexanebutyric acid and benzoic acid typically constitute organic acid compounds. Chloro- or fluorocarboxylic acids, such as trichloroacetic acid and trifluoroacetic acid, are also suitable. Sulphonic acids, sulphinic acids and phosphonic acids, as well as chloro or fluoro derivatives thereof, may also be suitable. Other organic acid compounds are compounds having a hydrogen atom close to one or more electron-withdrawing groups such as carbonyl (C=O), nitrile (CN), sulphone ($SO_2R$), nitro ($NO_2$) and phenyl groups, as well as chloro or fluoro derivatives thereof. Among the organic acid compounds according to this definition, mention may be made in particular of acetylacetone, trifluoroacetylacetone, 1,1,1,5,5,5-hexa-fluoropentane-2, 4-dione, acetonitrile, ethyl aceto-acetate, nitromethane, diphenylmethane, phenol and dimethyl sulphone. Copper compounds formed with organic acid compounds such as those mentioned above can be used in the process according to the present invention. The copper compounds formed with compounds such as acetylacetone, ethyl acetoacetate, acetic acid or cyclohexanebutyric acid and the chloro and fluoro derivatives thereof, are preferred. Copper (II) compounds are particularly preferred. Advantageously, the catalyst in the process according to the present invention is chosen from copper (II) acetate, copper (II) cyclohexanebutyrate and copper (II) acetylacetonate. Preference is most particularly given to the compound formed between copper (II) and acetylacetone (copper (II) acetylacetonate, abbreviated as Cu(acac)$_2$) as catalyst in the process according to the present invention.

In a first embodiment of the process according to the invention, the reaction is carried out in the presence of a solvent. Any solvent in which the reagents form the desired product in satisfactory yield can be used. Advantageously, the reaction solvent is an alcohol, a nitrile, an amide, a lactone, a trialkylphosphine oxide or another polar solvent. Oxygen-containing solvents (i.e. solvents in which the molecule contains at least one oxygen atom) are preferred.

Among the alcohols which can be used as reaction solvent are, in particular, methanol, ethanol, isopropanol and tert-butanol. Among the nitrites which can be used as reaction solvent are, in particular, aliphatic nitriles, in particular acetonitrile, propio-nitrile or adiponitrile, and aromatic nitriles, in particular benzonitrile or tolunitrile. Among the nitriles, propionitrile and adiponitrile are preferred. Among the amides which can be used as reaction solvent are linear amides such as N,N-dimethylacetamide and N,N-dimethylformamide, and cyclic amides such as N-methylpyrrolidone. Mention may also be made of hexamethylphosphoramide. Among the lactones which can be used as reaction solvent, mention may be made in particular of γ-butyrolactone. Among the trialkylphosphine oxides which can be used as reaction solvent, mention may be made in particular of the compounds of formula $(R_1R_2R_3)PO$, in which $R_1$, $R_2$ and $R_3$ represent identical or different, preferably linear C3–C10 alkyl groups. Tri (n-butyl)-phosphine oxide, tri(n-hexyl)phosphine oxide, tri(n-octyl)phosphine oxide, n-octyldi(n-hexyl)phosphine oxide and n-hexyldi(n-octyl)phosphine oxide and mixtures thereof are selected in particular. As other polar solvents, mention may also be made of 1,3-dimethyl-2-imidazolidinone, dimethyl sulphoxide and tetrahydrofuran. Preferably, the solvent is an amide or a trialkylphosphine oxide. Good results have been obtained in particular with N-methylpyrrolidone, with N,N-dimethylacetamide and with a mixture of tri (n-hexyl) phosphine oxide, tri (n-octyl)phosphine oxide, n-octyldi (n-hexyl)phosphine oxide and n-hexyldi (n-octyl)-phosphine oxide.

In a second, preferred embodiment of the process according to the invention, the reaction is carried out in the presence of an amine, an amide or a trialkylphosphine oxide as cocatalyst. As amides which can be used as cocatalyst, mention may be made of N-methyl-pyrrolidone and N,N-dimethylformamide. As trialkylphosphine oxides which can be used as cocatalyst, mention may be made of the same compounds as those which can be used as solvent in the first embodiment of the invention. An amine is preferably used as cocatalyst, in particular a primary amine. Aliphatic amines comprising from 3 to 25 carbon atoms are preferred. Aliphatic amines comprising from 3 to 22 carbon atoms are particularly preferred. As primary aliphatic amines which can be used in the process according to the invention, mention may be made of n-propylamine, isopropylamine, n-butylamine, isobutyl-amine, t-butylamine, pentylamine and isoamylamine. Among these amines, preference is given most particularly to amines in which the alkyl chain is branched, and more especially to tert-alkylamimes corresponding to the , al formula (I)

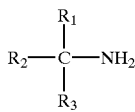

in which $R_1$, $R_2$ and $R_3$ represent C1–C8 alkyl groups. Amines corresponding to formula (I) are, in particular, t-butylamine and the tert-alkylamines Primenes® 81-R and JM-T, sold by Rohm & Haas Company. t-Butylamine is most particularly preferred.

The preferred catalyst-cocatalyst system according to the present invention is the system consisting of a copper (II) compound formed with an organic acid compound and of a primary amine in which the carbon atom next to the $NH_2$ group is a quaternary carbon atom, i.e. one with no hydrogen atoms. The catalyst-cocatalyst system formed by copper (II) acetyacetonate and t-butylamine is particularly preferred.

The haloalkanes used in the process according to the present invention are generally saturated organic compounds. They preferably have from one to three carbon atoms and preferably at least 2 chlorine atoms. They can also comprise other substituents such as other halogen atoms, alkyl groups or haloalkyl groups. As examples of haloalkanes according to the present invention, mention may be made of dichloromethane, chloroform, carbon tetrachloride, 1,1,1-trichloroethane and 1,1,1-trichloro-2,2,2-trifluoroethane. Carbon tetrachloride is most particularly preferred.

The olefin used in the process according to the present invention is generally ethylene, propylene or a butene, which are themselves optionally substituted with halogen atoms, alkyl or haloalkyl groups, nitrile (CN) groups or carboxylic acid (COOH) groups. Haloolefins are particularly suitable. As non-limiting examples of haloolefins, mention may be made of vinyl chloride, vinylidene chloride, trichloroethylene and various chloropropene isomers such as 1-chloro-1-propene, 2-chloro-l-propene and 3-chloro-1-propene. Excellent results have been obtained with vinyl chloride and 2-chloro-l-propene.

The halohydrocarbons obtained according to the process of the present invention generally belong to the chloropropane, chlorobutane or chloropentane family. The carbon atoms of the said chloropropanes, chlorobutanes and chloropentanes can also be substituted with other functional groups such as other halogen atoms (for instance bromine or iodine atoms), alkyl or haloalkyl groups, nitrile (CN) groups or carboxylic acid (COOH) groups. Chloropropanes and chlorobutanes which are not substituted with other functional groups are preferred.

Preferably, the halohydrocarbons obtained according to the process of the present invention correspond to the general formula $CnH_{(2n+2)-p}Cl_p$ in which n is an integer and has the value 3 or 4 and p is an integer which has the values 3 to 7. Examples of compounds obtained according to the process of the present invention are 1,1,1,3,3-pentachloropropane, 1,1,1,3,3-pentachlorobutane, 1,1,1,3,3-tetrachloro-propane, 1,1,3,3-tetrachlorobutane, 1,1,1,3,3,3-hexachloropropane and 1,1-dichloro-2-trichloromethylpropane. Among these compounds, 1,1,1,3,3-pentachloropropane, 1,1,1,3,3-pentachlorobutane and 1,1-dichloro-2-trichloromethylpropane are preferred. 1,1,1,3,3-pentachlorobutane and 1,1,1,3,3-pentachloropropane are most particularly preferred.

The molar ratio between the catalyst and the olefin is usually greater than or equal to 0.0001. Advantageously, it is greater than or equal to 0.001. Preferably, it is greater than or equal to 0.005. The molar ratio between the catalyst and the olefin is usually less than or equal to 1. Advantageously, it is less than or equal to 0.5. Preferably, it is less than or equal to 0.1.

The amount of solvent used in the first embodiment of the process according to the invention is not critical. However, too dilute a solution does not favour a high yield or a high degree of conversion. Preferably, the molar ratio of the solvent to the olefin is greater than or equal to 0.05. Advantageously, this ratio is greater than or equal to 0.1. The molar ratio of the solvent to the olefin is generally less than or equal to 30. Advantageously, it is less than or equal to 20. Preferably, this ratio is greater than or equal to 0.2 and less than or equal to 15. In a most preferred manner, it is greater than or equal to 1 and less than or equal to 10. In the reaction medium, the amount of solvent can vary, on a molar basis, from about 5 to about 500 times the amount of catalyst, preferably from about 10 to about 200 times.

In the second embodiment of the process according to the invention, the molar ratio between the cocatalyst and the olefin is generally greater than or equal to 0.01. Preferably, this molar ratio is greater than or equal to 0.05. Advantageously, this molar ratio is greater than or equal to 0.1. However, this molar ratio is usually less than or equal to 2. Preferably, this molar ratio is less than or equal to 1. Advantageously, this molar ratio is less than or equal to 0.5. The amount of cocatalyst used can vary, on a molar basis, from about 0.1 to about 25 times the amount of catalyst, preferably from about 0.5 to about 20 times.

The process according to the invention can be carried out in a continuous or batchwise manner.

It is understood that the amount of catalyst, of solvent or of cocatalyst used is expressed, in a batch-wise process, relative to the initial amount of olefin used, and, in a continuous process, relative to the stationary amount of olefin present in the reactor.

The molar ratio between the haloalkane and the olefin used can vary within a wide range. This ratio is generally greater than or equal to 0.1. Advantageously, this ratio is greater than or equal to 0.5. Preferably, it is greater than or equal to 1. Excellent results are obtained when this ratio is at least 1.2. Indeed, it has been observed, surprisingly, that it is possible, in the process according to the invention, to work with a ratio between the haloalkane and the olefin close to the stoichiometry without appreciably affecting the selectivity. Generally, this ratio is less than or equal to 15. Advantageously, this ratio is less than or equal to 10. Preferably, this ratio is less than or equal to 5.

Generally, the reaction takes place at a temperature greater than or equal to room temperature. Preferably, the temperature is greater than or equal to 500° C. Advantageously, the temperature is greater than or equal to 700° C. However, the temperature is generally less than or equal to 200° C. Preferably, the temperature is less than or equal to 175° C. Advantageously, the temperature is less than or equal to 150° C. Preference is most particularly given to a temperature less than or equal to 100° C.

The reaction time in a batchwise process or the residence time in a continuous process depend on various parameters such as the reaction temperature, the concentration of reagents and of catalyst in the reaction mixture and their molar ratios. In general, as a function of the parameters, the residence time or the reaction time can range from 5 minute to 10 hours. Advantageously, in a batchwise process, the reaction time is generally greater than or equal to 30 minutes with a preference for reaction times greater than or equal to 60 minutes. However, the reaction time is usually less than or equal to 10 hours, with a preference for reaction times of less than or equal to 8 hours.

The pressure is generally chosen so as to keep the reaction medium in liquid phase. The pressure used varies as a function of the temperature of the reaction medium. The pressure is usually greater than or equal to atmospheric pressure and less than or equal to 10 bar.

In the process according to the invention, the presence of a cocatalyst generally makes it possible to carry out the reaction in the absence of solvent, since the catalyst/cocatalyst system is usually soluble in the haloalkane used. However, the process according to the invention can also be carried out both in the presence of a solvent, in accordance with the first embodiment of the invention, and in the presence of a cocatalyst, in accordance with the second embodiment of the invention.

The halohydrocarbons obtained according to the process of the invention are precursors of the corresponding fluoro analogues, which can readily be obtained by treatment with hydrogen fluoride in the presence of a catalyst such as an antimony salt, a titanium salt, a tantalum salt or a tin salt.

The invention also relates to the catalytic telomerization systems used in the process according to the invention.

The examples below illustrate the invention in a non-limiting manner.

EXAMPLES 1–13

1,1,1,3,3-Pentachloropropane was prepared starting with vinyl chloride (VC) and carbon tetrachloride or 1,1,1,3,3-pentachlorobutane was prepared starting with 2-chloro-1-propene (2CPe) and carbon tetrachloride, by reaction between these reagents in the presence of an organocopper compound and an amine. To do this, the reagents, the catalyst and the cocatalyst were introduced into a 300 ml autoclave whose inner walls are lined with Teflon.

The apparatus was then closed hermitically, placed in a vertical oven and the temperature was increased gradually and maintained at 90° C. throughout the reaction. Stirring was ensured by a magnetic bar placed at the bottom of the autoclave. At the end of the reaction, the autoclave was allowed to cool and a sample of liquid was withdrawn by syringe and assayed by a chromatographic method in order to determine the degree of conversion of the olefin and selectivity towards halohydrocarbon. The results obtained are collated in Table I.

EXAMPLE 14 (comparative)

Example 12 was repeated, replacing the copper (II) acetylacetonate with CuCl. After reaction for 2 hours, the conversion of the 2-chloro-1-propene did not exceed 60%.

(1) $Cu(acac)_2$: copper (II) acetylacetonate
$Cu(TFacac)_2$: copper (II) 1,1,1-trifluoro-acetylacetonate
$Cu(HFacac)_2$: 1,1,1,5,5,5-hexafluoropentane-2,4-dione
$(CH_3CO_2)_2Cu$: copper (II) acetate
$(C_{10}H_{17}O_2)_2Cu$: copper (II) cyclohexanebutyrate (2): olefin/carbon tetrachloride/catalyst/cocatalyst molar ratio;

(3): the degree of conversion is the ratio, expressed as a percent, between the initial amount of olefin used minus the amount not converted and the amount used;

(4): the selectivity towards halohydrocarbon is the ratio, expressed as a percent, between the amount of halohydrocarbon formed and the amount of

TABLE I

| Ex. No. | Olefin | Catalyst[1] | Cocatalyst | Molar ratio[2] | Time (hours) | Conversion | Selectivity |
|---|---|---|---|---|---|---|---|
| 1 | VC | $Cu(acac)_2$ | t-butyalamine | 1/2.5/0.02/0.2 | 6 | 97 | 88 |
| 2 | VC | $Cu(acac)_2$ | t-butylamine | 1/2.5/0.02/0.2 | 1.5 | 94 | 88 |
| 3 | VC | $Cu(acac)_2$ | t-butylamine | 1/2.5/0.02/0.2 | 3 | 98 | 88 |
| 4 | VC | $Cu(acac)_2$ | t-butylamine | 1/1.2/0.02/0.2 | 6 | 97 | 81 |
| 5 | VC | $Cu(acac)_2$ | t-butylamine | 1/1.8/0.02/0.2 | 6 | 97 | 84 |
| 6 | VC | $Cu(TFacac)_2$ | t-butylamine | 1/2.2/0.02/0.17 | 1.5 | 99 | 86 |
| 7 | VC | $Cu(HFacac)_2$ | t-butylamine | 1/1.9/0.02/0.17 | 1.5 | 96 | 97 |
| 8 | VC | $Cu(acac)_2$ | Primene* 81-R[5] | 1/2.2/0.02/0.29 | 1.5 | 99 | 87 |
| 9 | 2CPe | $(CH_3CO_2)_2Cu$ | t-butylamine | 1/5/0.05/0.1 | 1 | 96 | 97 |
| 10 | 2CPe | $(CH_3CO_2)_2Cu$ | i-propylamine | 1/5/0.05/0.1 | 2 | 88 | 98 |
| 11 | 2CPe | $(C_{10}H_{17}O_2)_2Cu$ | i-propylamine | 1/5/0.05/0.1 | 2 | 92 | 98 |
| 12 | 2CPe | $Cu(acac)_2$ | i-propylamine | 1/5/0.05/0.1 | 2 | 82 | 93 |
| 13 | 2CPe | $Cu(HFacac)_2$ | Primene* JM-T[6] | 1/1.5/0.01/0.16 | 0.5 | 99 | 98 | halohydrocarbon which would have been formed if all of the olefin converted had generated the halohydrocarbon;

(5): the amine Primene® 81-R is a mixture of C12–C14 isomeric primary tert-alkylamines corresponding to the general formula (I), sold by the Rohm & Haas Company.

(6): the amine Primene® JM-T is a mixture of C16–C22 isomeric primary tert-alkylamines corresponding to the general formula (I), sold by the Rohm & Haas Company.

EXAMPLES 15–18

1,1, 1,3, 3-Pentachlorobutane was prepared starting with 2-chloro-1-propene and carbon tetrachloride in the presence of various solvents and copper (II) acetyl-acetonate as catalyst. The reaction time was 2 hours. The molar ratios of the reactants, the reaction temperatures and the results obtained are collated in Table II.

EXAMPLES 19–20

1, 1,3,3-Pentachlorobutane was prepared starting with 2-chloro-1-propene and carbon tetrachloride in the presence of copper (II) acetylacetonate as catalyst and a mixture of 4 trialkylphosphine oxides (tri(n-hexyl)-phosphine oxide, tri (n-octyl)phosphine oxide, n-octyl-di(n-hexyl)phosphine oxide and n-hexyldi (n-octyl)-phosphine oxide), sold by Cytec under the name Cyanex® 923. The reaction time was 2 hours. The molar ratios of the reagents, the reaction temperatures and the results obtained are also presented in Table II.

TABLE II

| Ex. | Solvent | 2-CPe/CCl$_4$/ Cu(acac)$_2$/solvent Molar ratio | Temperature | Conversion | Selectivity |
|---|---|---|---|---|---|
| 15 | N-methylpyrrolidone | 1/2/0.06/3.8 | 100° C. | 96 | 97 |
| 16 | N,N-dimethyl-acetamide | 1/3.5/0.06/4.1 | 90° C. | 67 | 99 |
| 17 | 1,3-dimethyl-2-imidazolidinone | 1/2.2/0.05/3.2 | 90° C | 46 | 97 |
| 18 | N,N-dimethyl-formamide | 1/1.9/0.06/5.7 | 100° C. | 72 | 96 |
| 19 | Cyanex ® 923 | 1/1.8/0.047/0.99 | 90° C. | 86 | 95 |
| 20 | Cyanex ® 923 | 1/5/0.05/0.24 | 90° C. | 88 | 95 |

What is claimed is:

1. A process for the manufacture of a halogenated hydrocarbon which is 1,1,1,3,3-pentachloropropane or 1,1,1,3,3,3-hexachloropropane and which comprises reacting tetrachloromethane and a halogenated olefin selected from vinyl chloride and vinylidene chloride, in which the reaction is carried out in the presence of 1 an organocopper (II) compound as catalyst; and 2 a polar solvent and/or a cocatalyst wherein said cocatalyst is amines, amides or trialkylphosphine oxides.

2. The process according to claim 1, wherein the organocopper compound used as catalyst is in the oxidation state (II).

3. The process according to claim 2, wherein the catalyst is copper (II) acetylacetonate.

4. The process according to claim 1, wherein the polar solvent is an alcohol, a nitrile, an amide, a lactone or a trialkylphosphine oxide.

5. The process according to claim 1, wherein the cocatalyst is an amine comprising from 3 to 25 carbon atoms.

6. The process according to claim 1, wherein the halohydrocarbon prepared is 1,1,1,3,3-pentachloropropane.

7. The process according to claim 1, wherein the halohydrocarbon prepared is 1,1,1,3,3,3-hexachloropropane.

8. The process as claimed in claim 1, wherein the organic acid compound is acetylacetone or chloro or fluoro derivatives thereof.

9. A process for the synthesis of fluorinated hydrocarbon selected from 1,1,1,3,3-pentofluoropropane and 1,1,1,3,3,3-hexofluoropropane conprising subjectingahalogenated hydrocarbon obtained according to the process according to claim 1, to a treatment with hydrogen fluoride.

10. The process according to claim 9, wherein the treatment with hydrogenfluoride is carried out in the presence of a catalyst.

11. The process according to claim 10, wherein the catalyst is antimony salt, titanium salt, tantalum salt or tin salt.

12. A process for the preparation of halohydrocarbons of the formula $C_nH_{(2n+2)-p}Cl_p$ in which n is an integer and has the value of 3 or 4 and p is an integer and has the values of 3 to 7 comprising at least 3 carbons atoms, by reaction between a haloalkane and an olefin, in which the reaction is carried out in the presence of (1) an organocopper (II)compound as a catalyst; and (2) a polar solvent and/or a cocatalyst wherein said cocatalyst is amines, amides or triallcylphosphine oxides.

13. The process according to claim 12, wherein the organocopper compound is a compound formed with an organic acid compound.

14. The process according to claim 13, wherein the organic acid compound is a carboxylic acid.

15. The process according to claim 13, wherein the organic acid compound is acetylacetone, ethyl acetoacetate, nitromethane, diphenylmethane, dimethyl sulphone, or chloro or fluoro derivatives thereof.

16. The process according to claim 12, wherein the catalyst is copper (II) acetylacetonate.

17. The process according to claim 12, wherein the polar solvent is an alcohol, a nitrile, an amide, a lactone or a trialkylphosphine oxide.

18. The process according to claim 12, wherein the cocatalyst is an amine comprising from 3 to 25 carbon atoms.

19. The process according to claim 12, wherein the halohydrocarbon prepared is 1,1,1,3,3-pentachloropropane.

20. The process according to claim 12, wherein the halohydrocarbon prepared is 1,1,1,3,3,3-hexachloropropane.

21. The process according to claim 1, wherein the organic acid compound is acetylacetone.

22. The process according to claim 13, wherein the organic acid compound is acetylacetone.

* * * * *

UNITED STATES PATENT AND TRADEMARK OFFICE
CERTIFICATE OF CORRECTION

PATENT NO. : 6,399,839 B1
DATED : June 4, 2002
INVENTOR(S) : Mathieu et al.

It is certified that error appears in the above-identified patent and that said Letters Patent is hereby corrected as shown below:

Column 7,
Line 46, delete "conprising" and insert -- comprising --.
Line 46, delete "subjectingahalogenated" and insert -- subjecting a halogenated --.

Signed and Sealed this

Sixteenth Day of July, 2002

*Attest:*

JAMES E. ROGAN
*Attesting Officer*   *Director of the United States Patent and Trademark Office*